United States Patent [19]

Reinherz et al.

[11] Patent Number: 4,550,086
[45] Date of Patent: Oct. 29, 1985

[54] MONOCLONAL ANTIBODIES THAT RECOGNIZE HUMAN T CELLS

[75] Inventors: Ellis L. Reinherz, Lincoln; Stuart F. Schlossman, Newton Centre, both of Mass.; Stefan C. Meuer, Alzey, Fed. Rep. of Germany

[73] Assignee: Dana-Farber Cancer Institute, Inc., Boston, Mass.

[21] Appl. No.: 466,948

[22] Filed: Feb. 16, 1983

[51] Int. Cl.$^4$ .................. G01N 33/50; G01N 33/58
[52] U.S. Cl. .................................. 436/506; 436/507; 436/508; 436/509; 436/548; 436/804; 436/811; 260/112 R; 435/7; 435/29; 435/68; 435/172.2; 424/1.1; 424/85; 935/93; 935/104; 935/108
[58] Field of Search ............... 436/547, 548, 506–509, 436/819; 424/1.1, 85, 177; 128/1.1; 260/112 R; 435/7, 29, 68, 70, 72, 240, 259, 804, 948; 935/93, 104, 108

[56] References Cited

U.S. PATENT DOCUMENTS 4,397,844 8/1983 Baschang et al. .................. 424/177
4,406,889 9/1983 Hartmann et al. .................. 424/177

OTHER PUBLICATIONS

Meuer, S. C. et al., J. Exp. Med., vol. 157, pp. 705–719 (1983).
Haskins, K. et al., J. Exp. Med., vol. 157, pp. 1149–1169 (1983).
Allison, J. P. et al., J. Immunology, vol. 129, pp. 2293–2300 (1982).
Lancki, D. W. et al., J. Exp. Med., vol. 157, pp. 921–935 (1983).
Samelson, J. E. et al., Proc. Natl. Acad. Sci., USA, vol. 80, pp. 6972–6976 (1983).
Sarimento, M. et al., J. of Inmunology, vol. 128, pp. 1676–1682 (1982).
Raeman, F. et al., Clin. and Exper. Immunology, vol. 45(3), pp. 475–479 (1981).
Reinherz, E. J. et al., Immunology Today, vol. 4(1), pp. 5–9 (1983).
Van Agthoven, A. et al., European J. Immunology, vol. 11, pp. 18–21 (01–1981).
Meuer, S. C. et al., Proc. Natl. Acad. Sci. USA, vol. 79, pp. 4395–4399 (7–1982).
Reinherz et al. (1982), Cell, vol. 30, pp. 735–743.
Meuer et al. (1982), Science, vol. 218, pp. 471–473.
Reinherz et al. (1980), New Eng. J. Med., vol. 303, p. 370.

*Primary Examiner*—Ben R. Padgett
*Assistant Examiner*—M. Moskowitz

[57] ABSTRACT

A monoclonal antibody which specifically binds to the surface recognition structure of a predetermined mature human T cell clone, which recognition structure renders the clone capable of acting as causative agent in a predetermined autoimmune disease, the monoclonal antibody being capable of specifically binding to the recognition structure of the clone to inhibit the ability of the clone to act as a causative agent in the predetermined autoimmune disease.

13 Claims, No Drawings

MONOCLONAL ANTIBODIES THAT RECOGNIZE HUMAN T CELLS

BACKGROUND OF THE INVENTION

This invention was made in the course of an award or grant from the National Institutes of Health, and the United States government therefore has rights in the invention.

This invention relates to immunology and, more specifically, to treating autoimmune diseases in which a mature human T cell acts as a causative agent.

A number of human autoimmune diseases, e.g. multiple sclerosis (m.s.), sarcoidosis, juvenile type diabetes mellitus, S.L.E. (Systemic Lupus Erythmatosis), thyroiditis, rheumatoid arthritis, ankyloses spondylitis, primary biliary cirrhosis, autoimmune hemolytic anemia, immune thrombocytopenia purpura, and myesthenia gravis are caused by a subpopulation of mature T cells which deleteriously recognize and attack a specific epitope, e.g., in the case of m.s., probably myelin or Schwann cells. (As used herein, "epitope" refers to any cell or cell product which can be recognized by a mature human T cell.)

Several multiple lineage surface molecules have recently been defined on the surfaces of mature human T cells, among them surface structures which have been designated T3, T4, and T8. The T3 surface structure is a glycoprotein having a molecular weight of about 20 kilodaltons (KD) (Reinherz et al. (1982) Cell 30, 735), is present on the surface of all functional mature human T cells (i.e., it is monomorphic), and is apparently necessary for the recognition of all given epitopes by T cells. Thus, a given monoclonal antibody (anti-T3) to T3 can block the ability of any functional T cell clone to recognize its target epitope, and contacting a heterogeneous population of mature human T cell clones with anti-T3 would therefore block the recognition function of all the clones ("clone", as used herein, refers to all mature human T cells which recognize the same epitope).

We have now discovered that each different mature T cell clone has on its surface a different proteinaceous structure (hereinafter its "recognition structure") which is responsible for that clone's ability to recognize its particular target epitope. The recognition structure of any given T cell clone is chemically different from the recognition structure of all other T cell clones, and recognizes a different specific epitope. For example, the T cell clone which acts as a causative agent in m.s. by attacking a particular epitope (probably myelin or Schwann cells) has a recognition structure which is chemically and immunologically different from that of the T cell clone which acts as a causative agent in sarcoidosis, and this difference is the basis for the ability of these different clones to recognize and attack different epitopes.

The recognition structure of each clone, although different from all others, has in common with that of other clones the characteristics of (1) being associated in the T cell membrane with the T3 glycoprotein, and of (2) being a heterodimer composed of a first proteinaceous component having a molecular weight of about 49 kilodaltons ("KD"), and a second proteinaceous component having a molecular weight of about 43 KD, the two components being covalently linked to each other via one or more disulfide bonds.

The present invention provides a monoclonal antibody which specifically binds to the surface recognition structure of any predetermined mature human T cell clone, which recognition structure renders the clone capable of acting as a causative agent in a predetermined autoimmune disease. The antibody does not bind to the surface recognition structure of any other mature human T cell clone. (For any given T cell clone, there is a potentially large number of such specifically binding monoclonal antibodies, all of which are subsumed under the singular "monoclonal antibody.")

The monoclonal antibody can render inactive the predetermined mature human T cell clone by specifically binding to the clone to inhibit its ability to act as a causative agent in the predetermined autoimmune disease. Such binding can either help cause the destruction of the clone, or can "blind" the clone, to render it unable to recognize and attack its target epitope.

The present invention also provides a method for producing such a specific monoclonal antibody, including the steps of providing a heterogeneous population of hybridomas, each producing a monoclonal antibody to a predetermined mature human T cell clone, selecting from the heterogeneous population a hybridoma producing a monoclonal antibody specific for the recognition structure on the T cell clone, and culturing the selected hybridoma to produce the monoclonal antibody.

In more detail, the steps involved in obtaining the desired specific monoclonal antibody are as follows. First there is provided a mature human T cell clone which is to be inactivated, e.g. the T cell clone involved in multiple sclerosis. The T cell clone is then used to immunize a mammal, e.g. a mouse. Appropriate lymphocytes (usually spleen cells) from the mammal are then harvested and fused to appropriate transformed cells (usually mouse or human myeloma cells), forming a heterogeneous population of hybridomas. The hybridoma population is then screened for production of monoclonal antibody, and antibody-producing hybridomas are then screened for those producing monoclonal antibody specific to the recognition structure of the immunizing T cell clone. This second screening step can be accomplished by contacting the monoclonal antibodies produced by the different hybridomas with a plurality of different mature human T cell clones, including the T cell clone used for immunization, and selecting the clone or clones reactive only with the immunizing clone, and discarding those reactive with any of the other clones (these produce antibodies which react with a structure, e.g. T3, on the immunizing clone which is found on the surface of other clones in addition to the immunizing clone). Enough different T cell clones must be used for screening to ensure specificity; generally at least 10, and preferably 20 or more, clones should be used. The selected hybridoma is then cultured to produce the desired specific monoclonal antibody.

The method by which the immunizing T cell clone (the clone involved in the autoimmune disease) is obtained will depend on the nature of the disease, e.g. the primary anatomical location where the deleterious attacking of the epitope by the T cell clone occurs. For example, since m.s. is primarily a disease of the brain, and the brain is in contact with the circulating cerebrospinal fluid, the T cell clone of interest will be present in that fluid. Furthermore, in most instances, the only activated T cell clone present in the fluid of an m.s. patient will be the T cell clone involved in the disease. Thus, to obtain the attacking T cell clone from an m.s.

patient, cerebrospinal fluid is withdrawn, e.g. by a simple lumbar puncture, and the T cell population is expanded, using conventional techniques, with Interleukin-2 ("IL-2"), which induces proliferation only in activated, and not resting, T cell clones, since only activated clones possess IL-2 receptors.

Another example of an anatomically limited autoimmune disease is sarcoidosis, in which an activated T4 clone attacks the lungs. To obtain the attacking clone, fluid can be obtained from the bronchial tree and IL-2 expansion carried out to proliferate the activated attacking clone.

In the case of an autoimmune disease in which the attacking T cell clone is present in the blood, which contains a huge number of mature T cell clones, IL-2 is also used, since almost all of those circulating clones will be resting clones which are not stimulated by IL-2.

As is clear from the above, in most cases it is not necessary to identify the epitope being attacked in order to isolate the attacking clone; in many cases the only activated T cell clone, or at least the major activated clone (the clone present in the greatest number) will be the attacking clone, which can be isolated without determining precisely what epitope it recognizes.

The monoclonal antibody produced by the above method can be contacted with the deleterious T cell clone to help destroy it or to blind it to inhibit its capacity to recognize and attack the target epitope it recognizes. The monoclonal antibody is thus useful in the treatment of an autoimmune disease, e.g. S.L.E., rheumatoid arthritis, or multiple sclerosis, in which a mature T cell clone to which the monoclonal antibody is specific acts as a causative agent by recognizing and attacking a particular epitope.

When administered to a patient having the autoimmune disease involving the T cell clone to which the monoclonal antibody is specific, the monoclonal antibody selectively binds to the clonal cells, either helping destroy them or blinding them so that they are unable to recognize and attack their target epitope, thus improving the medical condition of the patient.

The specificity of the monoclonal antibodies of the invention means that administration inactivates only the deleterious T cell clone, and has no effect on the patient's remaining mature T cells, which make up a crucial portion of the immune system. Furthermore, the fact that such specificity is a function of the particular epitope recognized by the recognition structure means that a particular monoclonal antibody will be effective against all patients having an autoimmune disease in which a mature T cell clone attacks the same epitope. The invention also permits the tailoring of a monoclonal antibody to any predetermined mature T cell clone of a given patient.

Any of the antibodies of the invention can be chemically linked to a cytotoxic agent to selectively deliver the toxin to the predetermined clone, without harming other cell types. Such cytotoxic agents can include chemotherapeutic agents, biological toxins such as ricin and mushroom toxins, radioactive agents, and photoactive toxins which are activated by UV light. Alternatively, the antibody can be used not to destroy but to blind the predetermined clone, in which case no cytotoxic agent is employed.

The method of administration of a monoclonal antibody of the invention will vary with individual circumstances, e.g. the particular disease being treated, as will the dosage and frequency of administration. Generally, the antibody will be mixed, prior to administration, with a non-toxic, pharmaceutically acceptable carrier substance, e.g. normal saline, and will be administered using any medically appropriate procedure, e.g., intravenous administration. The antibody will generally be present in the carrier in a concentration of between about 0.5 $\mu$g antibody/ml and 500 $\mu$g antibody/ml. The amount of antibody administered at one time will generally range between about 50 $\mu$g and 500 $\mu$g of antibody per kg of body weight. It will be desirable in some instances to administer the antibody to the patient in a series of more than one administration, and regular periodic administration will sometimes be required.

The following specific example is intended to more particularly point out the invention, without acting as a limitation upon its scope.

EXAMPLE

A monoclonal antibody specific to the surface recognition structure of a cytotoxic mature human T cell clone, designated $CT8_{III}$, was produced according to the following procedure.

First, the cytotoxic $CT8_{III}$ clone was generated from a human subject's mononuclear cells, which were stimulated in MLC with allogeneic Epstein Barr Virus (EBV)—transformed lymphoblastoid cells, of the cell line designated Laz 156. Cloning and recloning were carried out to propogate $CT8_{III}$, according to the method described in Meuer et al. (1982) P.N.A.S. USA 79, 4590. Optimal growth of T cell clones was obtained in the presence of a feeder cell suspension of irradiated autologous peripheral blood mononuclear cells plus irradiated Laz 156 cells in IL-2 conditioned media; proliferation also occurred in the presence of either irradiated Laz 156 or IL-2 conditioned medium.

The phenotype of $CT8_{III}$, as determined with a panel of monoclonal antibodies by means of indirect immunofluorescence, was T1−,T3+,T4−,T6−,T8+,T11+,T12+,Ia+. (+ means reactive, − means unreactive). The target specificity, an analyzed on a panel of HLA typed EBV-transformed target cells, was HLA-A3. The lympholytic function of $CT8_{III}$ could be blocked by anti-HLA but not by anti-Ia antibodies on the target cell level.

Balb/cJ mice were initially immunized IP with $5 \times 10^6$ $CT8_{III}$ cells in PBS. Ten days later a booster injection with $5 \times 10^6$ $CT8_{III}$ cells IP was performed. Three days prior to somatic fusion of immune splenocytes with NS-1 myeloma cells, two mice were injected IV and IP with a total of $5 \times 10^6$ $CT8_{III}$ cells. After sacrifice of the animals, immune splenocytes were obtained and fusion performed as described in Reinherz et al. (1979) *J. Immunol.* 123, 1312. Hybridoma growth was evident by 2 weeks. Subsequently, supernatants of hybridoma clones were screened for reactivity on $CT8_{III}$ by means of indirect immunofluorescence. Of 221 individual hybridomas which were established in HAT medium, 59 secreted monoclonal antibodies reactive with the immunizing clone $CT8_{III}$. Those which failed to produce antibodies reactive with $CT8_{III}$ were discarded.

Reactive supernatants were then screened on a large panel of cell types. These included: autologous and allogeneic resting peripheral blood cells (T cells clones, B cells, macrophages, granulocytes, platelets); thymocytes; autologous and allogeneic activated T cells (MLR lymphoblasts, Con A lymphoblasts, T cell lines (2–4 months old), 79 additional T cell clones derived from the same donor at CT8$_{III}$, autologous and allogeneic B cell lines (Laz 509, Laz 156, Laz 471), T cell tumor lines (CEM, Molt 4, HSB); and tumor lines of non-T cell lineage (K562,HL-60, Laz 221, KG1). It was found that 43 of the 59 CT8$_{III}$-reactive antibodies were also reactive with the autologous B lymphoblastoid cell line, Laz 509, and were therefore most likely directed at either alloantigens or other broadly distributed cell surface molecules. In contrast, the remaining 16 antibodies were reactive with the immunizing clone but lacked reactivity with B cells, macrophages, granulocytes, platelets, B lymphoblastoid lines, myeloid lines, and other hematopoietic lines.

Within the latter group, 7 antibodies were reactive with the 76 KD T8 surface structure (anti-T8$_{D-J}$), one recognized the 20 KD T3 molecule (anti-T3$_B$), and 6 were specific for activated but not resting T lymphocytes (anti-TA$_{1-6}$). In addition, two antibodies, termed anti-Ti$_{1A}$ and anti-Ti$_{1B}$, reacted exclusively with the CT8$_{III}$ clone and not with human thymocytes, with resting or activated human peripheral T cells (both autologous and allogeneic) or with the 79 additional individual alloreactivve T cell clones on the panel. Anti-Ti$_{1A}$ and anti-Ti$_{1B}$ were of the IgG$_1$ and IgM isotype, respectively. The hybridoma line producing anti Ti$_{1B}$ was deposited in the American Type Culture Collection, Rockville, Md., on Feb. 15, 1983, and was given ATCC Accession Number HB8213.

The specificity of anti-Ti$_{1A}$ and anti Ti$_{1B}$ was in contrast to the reactivity of anti-T3, which reacts with all mature T cell clones.

Further studies were performed on the specific anti-Ti$_{1A}$ and anti-Ti$_{1B}$ antibodies, which were provided in quantity needed for tests by cloning the hybrid cells producing them by limited dilution, and then injecting individual hybrid cells into pristine, primed Balb/cJ mice. The resulting ascitic fluid was used as a source of antibody.

In an antibody binding study employing CT8$_{III}$ and another mature T cell clone (designated CT8$_{IV}$) not reactive with anti-Ti$_{1A}$ or anti-Ti$_{1B}$, and from the same donor as CT8$_{III}$, all CT8$_{III}$ cells were shown to be reactive with anti-Ti$_{1A}$ and anti-Ti$_{1B}$, whereas CT8$_{IV}$ cells are unreactive with either antibody, as analyzed by indirect immunofluorescence on an Epics V cell sorter. In contrast, both CT8$_{III}$ and CT8$_{IV}$ expressed the 20 KD T3 molecule as defined by anti-T3 reactivity. Similar results to those obtained with CT8$_{IV}$ were found for the other 79 autologous clones. Reactivity was determined by means of individual immunofluorescence assays with goat anti-mouse F(ab')$_2$-FITC.

The following study demonstrated that anti-Ti$_{1A}$ and anti-Ti$_{1B}$ defined a surface structure on CT8$_{III}$ involved in epitope (antigen) recognition, and that these antibodies were capable of blocking such recognition. To study cell-mediated lympholysis and the effects of the antibodies on lympholysis, CT8$_{III}$ cells were incubated for various periods (30 min. to 18 hours) with anti-Ti$_{1A}$ and anti-Ti$_{1B}$ at several dilutions, prior to addition of $^{51}$Cr-labeled target cells. In parallel, the effects on lympholysis of several other T cell-specific monoclonal antibodies (anti-T3$_A$, -T3$_B$, -T8$_A$, -T8$_C$, and -T12) were investigated. The study was performed at an E/T ratio of 20:1 in V bottom microtiter plates (Falcon, Oxnard, CA) according to the method described in Reinherz et al. (1979) P.N.A.S. USA 76, 4061.

CT8$_{III}$ cells, in the absence of anti-Ti$_{1A \text{ or } Ti1B}$, were found to be highly efficient (greater than 50% lysis) in lysing the target cells, the HLA A 3+ B lymphoblastoid line Laz 156. The two specific antibodies Anti-Ti$_{1A}$ and -Ti$_{1B}$ both markedly inhibited CT8$_{III}$'s lympholytic capacity (less than 20% and less than 5% lysis, respectively). These inhibitor effects were observed at dilutions of ascites varying from 1:250 to 1:2500 and were evident after less than 30 min. of preincubation with CT8$_{III}$. The magnitude of inhibitory effect increased with the duration of preincubation. (Anti-T3$_{A,B}$ and anti-T8$_A$ also, not surprisingly, inhibited the lympholytic effect of CT8$_{III}$.)

In another lympholysis study designed to corroborate the indirect immunofluorescence results demonstrating that anti-Ti$_{1A}$ and -Ti$_{1B}$ were exclusively reactive with CT8$_{III}$, the inhibitor effects of these antibodies were tested against 5 lympholytic clones in addition to CT8$_{III}$. As shown in Table 1, below, these two specific antibodies were effective in inhibiting cell-mediated lympholysis only against CT8$_{III}$, and not against the other five clones. In contrast, the effects of anti-T3, anti-T4 and anti-T8 antibodies were not restricted to the CT8$_{III}$ clone. Anti-T3 monoclonal antibodies blocked all 5 lympholytic clones regardless of their T4+ or T8+ subset derivation or specificity; anti-T4$_A$ inhibited cytolysis by the T4+ clones CT4$_I$ and CT4$_{II}$ and had no effect on killing by the T8+ clones CT8$_I$, CT8$_{II}$ and CT8$_{III}$; and in a reciprocal fashion, anti-T8$_A$ and anti-T8$_B$ monoclonal antibodies inhibited killing of all three T8+ Clones but not the two T4 clones, CT4$_I$ and CT4$_{II}$.

TABLE I

INHIBITORY EFFECTS OF MONOCLONAL ANTIBODIES ON CML BY VARIOUS T CELL CLONES

| Monoclonal antibody | T cell clone | | | | |
|---|---|---|---|---|---|
| | CT4$_I$ | CT4$_{II}$ | CT8$_I$ | CT8$_{II}$ | CT8$_{III}$ |
| Anti-T3$_{A,B}$ | + | + | + | + | + |
| Anti-T4$_A$ | + | + | − | − | − |
| Anti-TB$_{A,B}$ | − | − | + | + | + |
| Anti-Ti$_{1A}$ | − | − | − | − | + |
| Anti-Ti$_{1B}$ | − | − | − | − | + |

Because some previous studies have indicated that some lympholytic cells not only specifically kill target cells but also proliferate to them in an antigen-specific fashion, the following proliferative study was performed to examine the effect of anti-Ti$_{1A}$ and -Ti$_{1B}$ on the antigen-specific proliferative capacity of CT8$_{III}$. CT8$_{III}$ cells were incubated for varying periods (30 min. to 18 hours) with the antibodies at several dilutions. Subsequently, untreated or antibody treated cells were plated, at 15,000 cells/well, into round-bottom microtiter plates (Costar, Cambridge, MA) along with either medium (RPMI 1640 supplemented with 10% human AB serum); irradiated Laz 156 cells (15,000 cells/well); IL-2 conditioned medium (final concentration 5%); or Laz 156 cells plus IL-2. (IL-2 containing supernatants were produced by stimulating whole peripheral blood mononuclear cells with phytohemagglutinin (PHA) and phorbol myristate (PMA) acetate in the presence of irradiated Laz 156 cells, as described in Meuer et al. (1982) P.N.A.S. USA 79, 4590.)

Following a 24 hour incubation at 37° C., the various cultures were pulsed with 0.2 Ci of tritiated thymidine (Schwartz Mann, Division of Becton Dickinson, Orangeburg, NY) and harvested 18 hours later on a Mash II apparatus (Microbiological Associates, Bethesda, MD). $^3$H-TdR incorporation was then measured in a Packard scintillation counter (Packard Instrument Co., Downer's Grove, IL).

The results of the proliferation study are shown in Table II below (each value represents the mean of triplicates). As shown therein, untreated $CT8_{III}$ cells proliferated to IL-2 containing supernatants as well as to the allogeneic cell line, Laz 156 to which they had been originally stimulated. Under these experimental conditions, antigen (Laz 156) was the stronger stimulus for $CT8_{III}$ cell proliferation, as judged by the greater $^3$H-TdR incorporation into $CT8_{III}$ with the former (12,000 cpm vs. 2,714 cpm). In addition, the induction of clonal proliferation by the combination of alloantigen and IL-2 was greater than with either alone (17,152 cpm). Pretreatment of $CT8_{III}$ with anti-$Ti_{1A}$ or anti-$Ti_{1B}$ markedly reduced antigen specific proliferation of the $CT8_{III}$ clone. Thus, whereas the untreated $CT8_{III}$ clone proliferated with greater than 12,000 counts of $^3$H-TdR to Laz 156, $CT8_{III}$ preincubated with anti-$Ti_{1A}$ or anti-$Ti_{1B}$ proliferated with less than 2,500 counts, a reduction in proliferation of greater than 80%. A similar reduction of proliferation was obtained with anti-$T3_B$. That these effects were not simply due to an inactivation of the $CT8_{III}$ clone as a result of antibody treatment is clear from the facts that 1) anti-T12 and anti-$T8_A$ had no inhibitory effects in this system (Table 2); and 2) the anti-$Ti_{1A}$, anti-$Ti_{1B}$ or anti-$T3_B$ treated $CT8_{III}$ clone had an augmented proliferative capacity to IL-2 containing supernatant (greater than 10,000 cpm vs less than 3,000 cpm). In contrast, anti-$T8_A$ has the ability to profoundly block the lympholytic effect of T8+ lympholytic clones, and completely lacks any inhibitory effect on antigen specific proliferation.

cence on a Epics V fluorescence activated cell sorter with a panel of monoclonal antibodies.

Prior to modulation, all $CT8_{III}$ cells were found to be reactive with anti-$T3_A$, anti-$Ti_{1A}$, anti-$Ti_{1B}$ and anti-$T8_A$. In contrast, after modulation with anti-$T3_B$, T3 antigen was no longer detectable. Anti-$T3_B$ induced modulation also resulted in loss of the anti-$Ti_{1A}$ and anti-$Ti_{1B}$ surface epitopes. That this was not a nonspecific effect is evident from the observation that the T8 antigen density was uninfluenced by this process.

Incubation of $CT8_{III}$ cells with either anti-$Ti_{1A}$ or anti-$Ti_{1B}$ had identical effects: in all cases T3, $Ti_{1A}$ and $Ti_{1B}$ molecules comodulated. These results indicate that the molecules defined by anti-T3, anti-$Ti_{1A}$ and anti-$Ti_{1B}$ are functionally and phenotypically linked on the cell surface of the $CT8_{III}$ cione.

To investigate the relationship of the epitope defined by anti-T3 and those defined by anti-$Ti_{1A}$ and anti-$Ti_{1B}$ further, both competitive antibody binding inhibition studies and immunoprecipitations were performed.

For these studies, directly FITC labelled purified monoclonal antibodies (anti-$T3_A$, anti-$Ti_{1A}$, anti-$Ti_{1B}$) were prepared. All studies were performed at 4° C. in order to prevent modulation of cell surface antigens. In the first incubation step, $CT8_{III}$ cells were incubated with saturating amounts of one or another unlabelled monoclonal antibody for 30 min. Then the cells were washed twice and incubated with directly FITC labelled monoclonal antibody (30 min) prior to FACS analysis. Unlabelled anti-$T3_A$ and anti-$T3_B$ inhibited subsequent binding of directly FITC labelled anti-$T3_A$, whereas anti-$Ti_{1A}$ and anti-$Ti_{1B}$ did not. In a reciprocal fashion, unlabelled anti-$T3_A$ or anti-$T3_B$ failed to inhibit subsequent binding of directly FITC labelled anti-$Ti_{1A}$ or anti-$Ti_{1B}$. In contrast, either unlabelled anti-$Ti_1$ antibody was inhibitory for FITC labelled anti-$Ti_{1A}$ or anti-$Ti_{1B}$. Under no circumstances did unlabelled anti-$T8_A$ block binding of directly FITC labelled anti-$T3_A$, anti-$Ti_{1A}$, or anti-$Ti_{1B}$. Taken together, these findings

TABLE II

INFLUENCES OF MONOCLONAL ANTIBODIES ON PROLIFERATIVE RESPONSES OF CLONE $CT8_{III}$

| Stimulus | Untreated | Anti-$Ti_{1A}$ | Anti-$Ti_{1B}$ | Anti-$T3_B$ | Anti-$T8_A$ | Anti-T12 |
|---|---|---|---|---|---|---|
| Medium | 41 ± 23 | 139 ± 36 | 206 ± 54 | 92 ± 34 | 65 ± 27 | 23 ± 20 |
| IL 2 | 2714 ± 135 | 10927 ± 1520 | 15009 ± 1049 | 13417 ± 1520 | 2525 ± 327 | 2459 ± 476 |
| Laz 156 | 12295 ± 317 | 2117 ± 438 | 1169 ± 207 | 776 ± 99 | 11756 ± 817 | 10956 ± 357 |
| IL 2 + Laz 156 | 17152 ± 471 | 14399 ± 1005 | 15953 ± 2176 | 15739 ± 1377 | 15389 ± 2176 | 14992 ± 790 |

The observation that anti-T3, anti-$Ti_{1A}$, and anti-$Ti_{1B}$ all inhibited antigen specific proliferation, lympholytic function, and enhanced IL-2 responsiveness of $CT8_{III}$, suggested that there might be a relationship between the cell surface structures defined by these antibodies. In this regard, previous studies indicated that binding of anti-T3 antibodies to T cells at 37° C. resulted in selective modulation and external shedding of the T3 molecular complex without affecting cell viability or altering expression of other known T cell surface structures including T1, T11, T12, or T8 surface molecules. To determine whether anti-T3 induced modulation produced changes in surface expression of detectable $Ti_{1A}$ or $Ti_{1B}$ molecules, $CT8_{III}$ cells were first incubated in final culture medium RPMI 1640 plus 12% human AB serum with anti-$T3_B$ for 18 hours at 37° C., then washed to remove free monoclonal antibody, and subsequently, cell reactivity analyzed by indirect immunofluoresare evidence that there is a single surface epitope recognized by both anti-$Ti_{1A}$ and anti-$Ti_{1B}$.

To biochemically define the surface structure detected by anti-$Ti_{1A}$ and anti-$Ti_{1B}$, $CT8_{III}$ cells were labelled by lactoperoxidase technique with $^{131}$I (New England Nuclear, Boston, MA) and immunoprecipitates from solubilized membranes subjected to SDS polyacrylamide gel electrophoresis, as follows. To $20 \times 10^6$ cells suspended in 1 ml PBS were added successively 10 μl glucose (0.5 Mol/l), 5 μl NaI ($5 \times 10^4$ Mol/l), 10 μl lactoperoxidase (2 mg/ml), 1 mCi Na $^{131}$I and 20 μl glucose oxidase (7.5 mU/ml). This mixture was incubated for 15 min at room temperature followed by addition of 100 μl NaI (1 Mol/l). After an additional 2 min of incubation, cells were washed 4 times in Hanks balanced salt solution. The final pellet was lysed in 500 μl 1:5 diluted RIPA stock solution containing 1% Triton X-100 (RIPA stock solution: 0.1 Mol/l $NaH_2PO_4$, 1 m Mol/l PMSF, 10 m Mol/l EDTA, 10 m Mol/l EGTA, 10 mMol NaF, 1% deoxycholate sodium salt, aprotinin 200 KIU/ml, pH 7.2). The suspension was centrifuged for 5 min at 1120 g and the resulting supernatant precleared twice utilizing monoclonal antibody anti-T6 covalently linked to CnBr activated Sepharose 4B (Pharmacia, uppsala, Sweden) each for 30 min at 4° C. and subsequently centrifuged 5 min at 1120 g. Precleared lysates were incubated with monoclonal antibodies bound to CnBr activated Sepharose 4B for 60 min at 4° C. The resulting precipitate was subsequently washed 5 times in RIPA solution (stock 1:10 diluted)+1% Triton X-100 resuspended in gel buffer (0.125 Mol/l Tris-HCl pH 6.8 containing 10% glycerol, 3% SDS and 5% 2-mercaptoethanol) and boiled for 5 min. SDS-PAGE was performed on a continuous vertical slab gel (12.5% polyacrylamide) for 14 hours according to a modification of the procedure described in Laemmli (1970) Nature 227, 680.

As a control, $CT8_{IV}$ (unreactive with anti-$Ti_{1A}$ and anti-$Ti_{1B}$) was tested in parallel. Molecular weights were estimated from the mobility of radioactive molecular weight markers (New England Nuclear) (Cytochrome C, 12,300; lactoglobulin A, 18,367; carbonic anhydrase, 30,000; ovalbumin, 46,000; phosphorylase AB, 97,400). Under reducing conditions, anti-$Ti_{1A}$ precipitated two distinct bands of approximately 49KD and 43KD, respectively from the $CT8_{III}$ clone, but not the irrelevant $CT8_{IV}$ clone. In a parallel fashion, anti-$Ti_{1B}$ precipitated identical structures from the same $CT8_{III}$ clone but not the irrelevant $CT8_{IV}$ clone. Both the inability of anti-$Ti_{1A}$ and -$Ti_{1B}$ to inhibit anti-T3 cell surface binding and the present biochemical data are consistent with the fact that these two specific antibodies are directed at a different glycoprotein than the major 20KD glycoprotein defined by anti-T3 antibodies.

To determine whether the 49KD and 43KD components of the $CT8_{III}$ surface recognition structure to which anti-$Ti_{1B}$ specifically reacted were disulfide linked on the membrane of $CT8_{III}$, the anti-$Ti_{1B}$ precipitates were run in SDS-PAGE under non-reducing conditions, i.e., 2-mercaptoethanol was omitted. Under such conditions, anti-$Ti_{1B}$ immunoprecipated a single broad band at 80-90KD, indicating that the surface recognition structure is a heterodimer composed of subunits of molecular weight 49KD and 43KD, joined by disulfide bonds.

As was mentioned above, the T3 structure and the recognition structure are associated on $CT8_{III}$. To define the relationship of these structures further, anti-T3 monoclonal antibody was used to immunoprecipitate surface material from $CT8_{III}$ and 6 additional $^{125}I$ labelled antigen responsive clones with differing specificities which were derived from the same donor. The precipitations were characterized on SDS-PAGE analysis and compared to those obtained with anti-$Ti_{1B}$.

The results obtained for $CT8_{III}$ and $CT8_{IV}$ showed that the material precipitated with anti-T3 from the two clones appeared to be similar, the major protein band having a molecular weight of about 20KD. In both cases there were also bands defining proteins of molecular weights of 49KD and 43KD. These appear to be identical in size to the protein found in the anti-$Ti_{1B}$ immunoprecipitate from $CT8_{III}$. As expected, anti-$Ti_{1B}$ did not precipitate any detectable bands from the $Ti_{1B}$ unreactive clone $CT8_{IV}$.

To determine whether the higher molecular weight proteins in the anti-T3 immunoprecipitates from $CT8_{III}$ were, in fact, related to those defined by the anti-clonotypic antibody anti-$Ti_{1B}$, a series of sequential immunoprecipitation studies were performed with the $Ti_{1B}$ unreactive clone $CT8_{II}$ and the $Ti_{1B}$ reactive clone $CT8_{III}$ ($CT8_{II}$ was a mature lympholytic T cell taken from the same individual as $CT8_{III}$.) For the sequential precipitation studies, radiolabelled cell lysates were precleared 2 times with anti-T12-Sepharose or anti-$Ti_{1B}$-Sepharose, incubated at 4° C. for 60 min with anti-T3, and precipitated with protein A Sepharose-rabbit antimouse Ig.

Preclearing of externally labelled cell lysates from $CT8_{II}$ with anti-T12 or anti-$Ti_{1B}$ did not affect the subsequent density of the higher molecular weight bands in the anti-T3 immunoprecipitation on SDS-PAGE analysis. In contrast, when labelled cell lysates from the $Ti_{1B}$ reactive clone $CT8_{III}$ were precleared with anti-$Ti_{1B}$ prior to anti-T3 immunoprecipitation, there was a marked reduction in the higher molecular weight bands in comparison to the lysates of $CT8_{III}$ precleared with the unrelated anti-T12 antibody. Since anti-$Ti_{1B}$ precipitated little, if any, material in the range of the 20KD T3 molecule, it is likely that the monoclonal antibody dissociates the 49/43KD molecule from the 20/25KD molecules when it binds to the former. The above results provide strong evidence that the 49KD and 43KD proteins found in anti-T3 immunoprecipitates of $CT8_{III}$ cell lysates comprise the recognition structure recognized by anti-$Ti_{1B}$. All of the results also indicate that clonotypic structures exist on all mature T cell clones and are associated with the 20 and 25KD T3 molecules. The latter findings suggest that anti-T3 could be used as a probe to isolate and compare these clonotypic structures on a series of other clones where no anti-clonotypic antibodies reactive directly with the 49/43KD structure yet exists.

The finding that $Ti_{1A}$ and $Ti_{1B}$ were present on $CT8_{III}$ and none of 79 additional clones from the same individual is evidence that they define a structure with a variable domain. To determine whether the 49/43KD structure on clones of different specificities do, in fact, differ from one another, 2D gel electrophoresis and peptide map analysis of anti-T3 immunoprecipitates from multiple externally labelled clones were compared. The labeled clones were $CT8_{II}$ and $CT8_{III}$, two autoreactive lympholytic clones $AT4_{I}$ and ($AT4_{III}$); and 5 additional T4+ and T8+ T cell clones.

For 2 dimensional gel electrophoresis, anti-T3 precipitates from lysates of the above $^{125}I$ labelled clones were dissolved in isoelectric focusing sample buffer (9.5M urea, 2% triton X-100, 2% ampholytes; pH 3.5-10, pH 4-6, and pH 5-8; ratio 1:1.2:4) and analyzed by isoelectric focusing gels and a SDS-PAGE system according to the methods described in Garrels (1979) *J. Biol. Chem.* 254, 7961 and O'Farrel (1975) *J. Biol. Chem.* 250, 4007.

Peptide mapping by limited proteolysis employed the method described in Cleveland et al. (1977) *J. Biol. Chem.* 252, 1102, with a modification that the first dimensional separation was performed in 12.5% SDS-polyacrylamide gel tubes. After being subject to electrophoresis, the latter was incubated for 30 min at 20° C. with 100 mM Tris-HCl, pH 8.6 and 100 g per ml protease [either chymotrypsin (Boehringer Mannheim, Indianappolis, IN) or staph V8 (Miles Laboratory, Elkhart, IN)]. These were then applied to 12.5% polyacrylamide gels containing an identical concentration of protease in the stacking gel.

In the 2D gel analyses and isoelectric focusing, the 20KD glycoprotein within the anti-T3 immunoprecipitate resolved into 5 spots in this system whereas the 25KD glycoprotein appeared as at least two separate spots which were more basic than the former. From the 2D analysis, it was concluded that these structures on $AT4_I$ and $AT4_{III}$ clones are similar, if not identical. Comparable results were also obtained with the five additional T4+ and T8+ T cell clones tested. In contrast, the 49/43KD clonotypic structures showed considerable variability. For example, the 43KD protein in the immunoprecipitate of $AT4_I$ had a more acidic isoelectric point than the 43KD protein from $AT4_{III}$. Some charge variability was noted in the 49KD protein from these clones.

From the above results it can be concluded that among individual T cell clones the 20 and 25 KD proteins show little heterogeneity whereas the 49/43KD heterodimer shows considerable isoelectric point variability.

To define whether this was due to variablility in the polypeptide chains themselves, the 49/43KD structures within anti-T3 immunoprecipitates of individual clones were obtained, digested, and peptide maps produced. The results indicated that there is one major chymotryptic fragment generated from the 49KD structure. This appears identical for each of these clones. In contrast, chymotryptic fragments from the 43KD protein of $CT4_{II}$ and $CT8_{III}$ are distinct. The peptide map of $CT8_{III}$ shows a single major cleavage product and multiple minor fragments whereas that from $CT4_{II}$ contained a different peptide fragment. The latter fragment is clearly not present in the map of the 43KD protein from $CT8_{III}$.

Analysis of the 49 and 43KD glycoproteins from 4 additional clones showed considerable heterogeneity in chymotriptic as well as staph V8 maps. However, while variability was always evident within the 43KD structure, the possibility could not be ruled out that some variability might also exist within the 49KD molecule as well. In contrast, in no instance did one detect variability within the 20/25KD glycoproteins of the anti-T3 immunoprecipitates.

Other embodiments are within the following claims.

We claim:

1. A mammalian monoclonal antibody which specifically binds to the surface recognition structure of a mature human T lymphocyte clone, said T lymphocyte clone deleteriously recognizing a specific target epitope and thereby acting as a causative agent in an autoimmune disease, said surface recognition structure comprising a glycoprotein heterodimer responsible for said clone's ability to recognize said epitope, said monoclonal antibody being capable of specifically binding to said recognition structure of said clone and thereby inhibiting the ability of said clone to act as a causative agent in said autoimmune disease.

2. The monoclonal antibody of claim 1 wherein said surface recognition structure comprises a first component having a molecular weight of about 49 kilodaltons and a second component having a molecular weight of about 43 kilodaltons, said first and second components being covalently linked to each other via disulfide bonds.

3. The monoclonal antibody of claim 1, wherein said heterodimer can co-precipitate with the T3 surface structure glycoprotein having a molecular weight of about 20 kilodaltons when said T3 surface structure glycoprotein is immunoprecipitated using a monoclonal antibody specific therefor for said 20 kilodalton T3 surface structure.

4. The monoclonal antibody of claim 1 wherein said autoimmune disease is Systemic Lupus Erythmatosis.

5. The monoclonal antibody of claim 1 wherein said autoimmune disease is juvenile diabetes mellitus.

6. The monoclonal antibody of claim 1 wherein said autoimmune disease is rheumatoid arthritis.

7. The monoclonal antibody of claim 1 wherein said autoimmune disease is multiple sclerosis.

8. The monoclonal antibody of claim 1 wherein said antibody is chemically linked to a cytotoxic agent.

9. The monoclonal antibody of claim 8 wherein said cytotoxic agent is a chemotherapeutic agent.

10. The monoclonal antibody of claim 8 wherein said cytotoxic agent is a photoactivated toxic agent.

11. The monoclonal antibody of claim 8 wherein said cytotoxic agent is a radioactive agent.

12. A method of producing the monoclonal antibody of claim 1 comprising providing a plurality of hybridoma cells, each producing a murine monoclonal antibody capable of specifically binding to said mature human T lymphocyte clone, selecting from said cells a hybridoma cell producing an antibody which is specific to said surface recognition structure on said mature T lymphocyte clone, and culturing said selected hybridoma to produce said monoclonal antibody.

13. A method of reducing the ability of a mature human T lymphocyte clone to recognize and attack the epitope for which its surface recognition structure is specific comprising producing a murine monoclonal antibody capable of specifically binding to said surface recognition structure; and contacting said T lymphocyte clone with said monoclonal antibody, in an amount sufficient to cause said reduction in said ability.

* * * * *

UNITED STATES PATENT AND TRADEMARK OFFICE
CERTIFICATE OF CORRECTION

PATENT NO. : 4,550,086
DATED : October 29, 1985
INVENTOR(S) : Ellis L. Reinherz et al.

It is certified that error appears in the above-identified patent and that said Letters Patent are hereby corrected as shown below:

Column 11, claim 1, line 46, insert "murine" before "mammalian";

Column 11, claim 1, line 47, insert before "surface", --clonotypic--;

Column 11, claim 1, line 51, insert before "surface", --clonotypic--;

Column 12, claim 3, line 15, delete "therefor".

Signed and Sealed this

Nineteenth Day of August 1986

[SEAL]

Attest:

*Attesting Officer*

DONALD J. QUIGG

*Commissioner of Patents and Trademarks*